(12) United States Patent
Piasecki

(10) Patent No.: US 9,289,223 B2
(45) Date of Patent: Mar. 22, 2016

(54) SURGICAL GUIDE INSTRUMENT AND SYSTEM FOR ACL RECONSTRUCTION AND METHOD OF USING SAME

(71) Applicant: Dana P. Piasecki, Charlotte, NC (US)

(72) Inventor: Dana P. Piasecki, Charlotte, NC (US)

(73) Assignee: DANAMED, INC., Charlotte, NC (US)

( * ) Notice: Subject to any disclaimer, the term of this patent is extended or adjusted under 35 U.S.C. 154(b) by 0 days.

(21) Appl. No.: 14/293,404

(22) Filed: Jun. 2, 2014

(65) Prior Publication Data

US 2014/0303630 A1 Oct. 9, 2014

Related U.S. Application Data

(63) Continuation-in-part of application No. 13/662,475, filed on Oct. 27, 2012, now Pat. No. 8,821,509.

(51) Int. Cl.
| | |
|---|---|
| *A61B 17/17* | (2006.01) |
| *A61B 17/16* | (2006.01) |
| *A61B 17/88* | (2006.01) |
| *A61F 2/08* | (2006.01) |

(52) U.S. Cl.
CPC ......... *A61B 17/1764* (2013.01); *A61B 17/1714* (2013.01); *A61B 17/8872* (2013.01); *A61B 17/1796* (2013.01); *A61B 17/8897* (2013.01); *A61F 2/0805* (2013.01)

(58) Field of Classification Search
CPC ........... A61B 17/1764; A61B 17/1714; A61B 17/1796; A61B 17/8872; A61B 17/8897; A61F 2/0805
USPC ........... 606/108, 88, 96–98, 103, 53, 232, 80, 606/79, 87, 86 R; 623/20.35, 20.14, 20.32, 623/13.11, 13.14, 13.12

See application file for complete search history.

(56) References Cited

U.S. PATENT DOCUMENTS

| | | |
|---|---|---|
| 4,509,516 A | 4/1985 | Richmond |
| 4,883,048 A | 11/1989 | Purnell et al. |
| 4,966,143 A | 10/1990 | Meinershagen |
| 4,997,434 A | 3/1991 | Seedhom et al. |
| 5,089,003 A | 2/1992 | Fallin et al. |
| 5,163,940 A | 11/1992 | Bourque |

(Continued)

OTHER PUBLICATIONS

International Search Report and Written Opinion issued by the ISA/ U.S. Receiving Office, from corresponding patent application Serial No. PCT/US13/65882; dated Jan. 14, 2014; 10 pages.

(Continued)

*Primary Examiner* — Pedro Philogene
(74) *Attorney, Agent, or Firm* — Barbara A. Wrigley; Fox Rothschild LLP

(57) ABSTRACT

A system for performing anterior cruciate ligament reconstructions is provided. The system includes a surgical guide instrument defining an elongate body having a hand-graspable handle and a head section including a distal phalange and a proximal open-faced slot. The distal phalange is contoured to anatomically conform to the femur and includes a notch section engageable with the intercondylar notch. The open-faced slot includes a stop member. The system further includes a guide wire operably receivable by a guide wire sheath to form a guide wire assembly. The guide wire assembly is received by the open-faced slot wherein the stop member is structured to stop the sheath from exiting the slot. The surgical guide instrument can direct the guide wire to an anatomic position on the femur and ensure a safe and usable femoral tunnel.

21 Claims, 16 Drawing Sheets

(56) References Cited

U.S. PATENT DOCUMENTS

| | | | |
|---|---|---|---|
| 5,269,786 A | 12/1993 | Morgan | |
| 5,350,383 A * | 9/1994 | Schmieding et al. | 606/96 |
| 5,496,326 A | 3/1996 | Johnson | |
| 5,520,693 A * | 5/1996 | McGuire et al. | 606/86 R |
| 5,643,273 A * | 7/1997 | Clark | 606/96 |
| 5,713,897 A | 2/1998 | Goble et al. | |
| 5,810,864 A | 9/1998 | Schaller | |
| 5,879,353 A | 3/1999 | Terry | |
| 5,891,147 A | 4/1999 | Moskovitz et al. | |
| 6,171,310 B1 | 1/2001 | Giordano et al. | |
| 7,235,074 B1 | 6/2007 | Sklar | |
| 7,458,975 B2 | 12/2008 | May et al. | |
| 8,444,652 B2 | 5/2013 | Amis et al. | |
| 8,814,935 B2 * | 8/2014 | Paulos | 623/11.11 |
| 2006/0089633 A1 * | 4/2006 | Bleich et al. | 606/32 |
| 2009/0248029 A1 | 10/2009 | Paulos | |
| 2010/0249497 A1 | 9/2010 | Peine et al. | |
| 2011/0071544 A1 | 3/2011 | Steger, Jr. et al. | |
| 2012/0004731 A1 | 1/2012 | Viker | |
| 2012/0265205 A1 | 10/2012 | Steiner et al. | |
| 2013/0184610 A1 * | 7/2013 | Bourque et al. | 600/585 |

OTHER PUBLICATIONS

International Search Report and Written Opinion issued by the I.S. A./U.S. Receiving Office, regarding corresponding application Serial No. PCT/US2014/060846, dated Feb. 2, 2015, 9 pages.

* cited by examiner

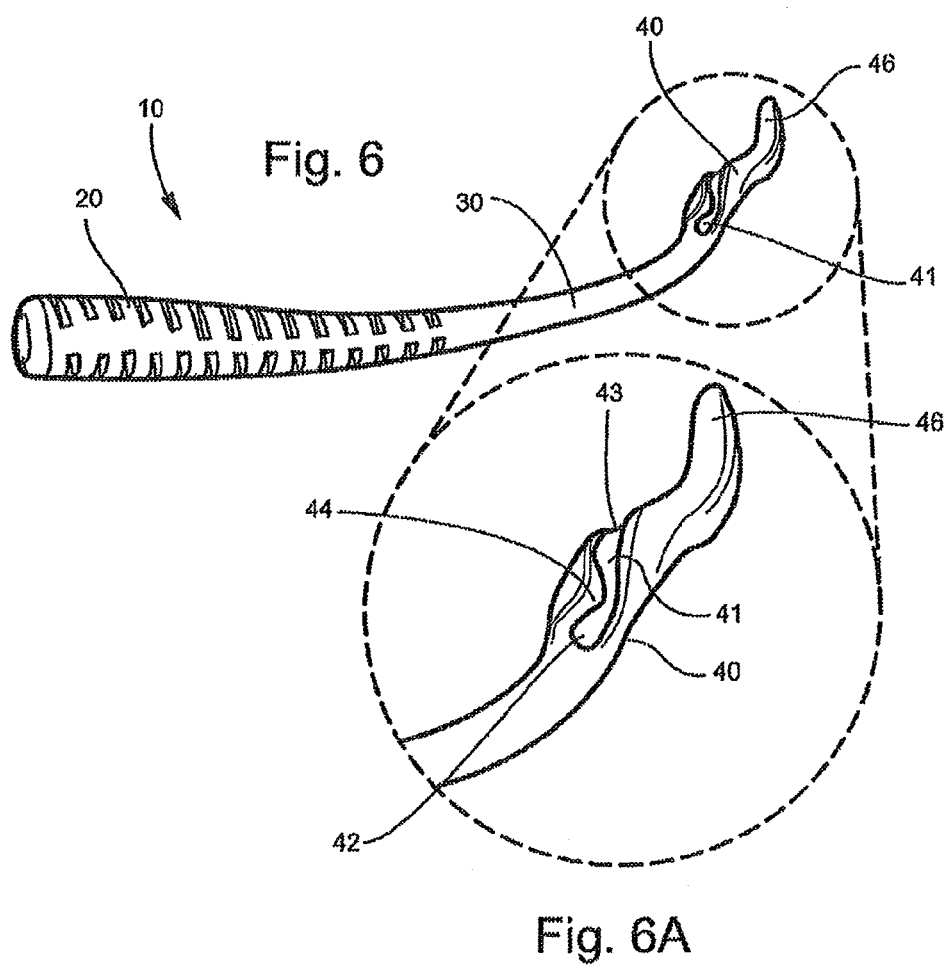

SURGICAL GUIDE INSTRUMENT AND SYSTEM FOR ACL RECONSTRUCTION AND METHOD OF USING SAME

CROSS-REFERENCE TO RELATED APPLICATIONS

This application is a continuation-in-part of co-pending U.S. patent application Ser. No. 13/662,475, filed on Oct. 27, 2012, the entirety of which is incorporated by reference herein.

FIELD OF THE INVENTION

The present invention relates to a surgical guide instrument and a system for use in anterior cruciate ligament reconstruction procedures. In particular, the surgical system includes an ACL surgical guide instrument, a guide wire and a guide wire sheath.

BACKGROUND OF THE RELATED ART

A torn ACL typically cannot be repaired because it cannot heal. Therefore it must be reconstructed. ACL reconstruction involves replacing of the ligament with a similarly sized piece of tissue, known as a graft. After healed in position, the graft is intended to function like a normal ACL.

A commonly performed technique for reconstructing the ACL is the "transtibial" technique. In this technique, a bone tunnel is drilled through the tibia such that the tunnel enters the knee joint where the ACL would normally attach. A drill guide is then inserted through the drilled tunnel to position a guide wire on the femur. A cannulated reamer is used to drill a second bone tunnel on the femur. A graft is then passed through the tibial tunnel, across the joint space and into the femoral tunnel. When the graft is fixed in position, it connects the two normal attachment points of the original ACL, thereby replicating the function of a normal ACL.

Recent medical studies suggest potential problems associated with the transtibial technique. The primary limitation of conventional devices is the tibial tunnel itself; because the tibial tunnel is a rigid cylinder, it limits mobility of conventional instrumentation, making it nearly impossible to reach the ideal position on the femur for attaching the graft.

An alternative to the transtibial technique is the AM portal technique. In this technique, a drill guide is passed through a small incision at the joint line, known as the anteromedial (AM) portal, rather than through the tibial tunnel. The drill guide directs the guide wire to an anatomic position on the femur. Conventional guides require that the guide wire be inserted through the AM portal incision together with the guide. To safely direct the guide wire, the knee must be hyper-flexed thus requiring additional staff in the operating room. Additionally, the AM portal technique is more difficult because the hyper-flexed knee decreases the surgeon's ability to see inside the joint space. Another problem with this technique is that it has been shown to direct the guide wire out of the knee in such a way that the trajectory of the guide wire results in a much less usable femoral tunnel. In other words, the insertion point of the wire may be anatomically correct, but the trajectory of the wire is frequently incorrect which may hinder the surgeon's ability to adequately fix the graft on the femoral side.

Many practicing orthopedic surgeons were trained to perform ACL reconstructions using the transtibial technique, however, most orthopedic surgeons perform a relatively small number of ACL reconstruction surgeries each year. As such, the use of an unfamiliar and more complicated technique is less desirable for many practitioners. Moreover, conventional transtibial instrumentation has—to date—not been able to accomplish anatomic graft positioning on the femur.

Therefore, what is needed is a new surgical system that will address the aforementioned problems. In particular, what is needed is a surgical system that allows orthopedic surgeons to perform ACL reconstructions utilizing the principles of the relatively easier transtibial technique, while providing the improved graft positioning associated with the more technically difficult AM portal technique.

SUMMARY OF THE INVENTION

The aforementioned problems are addressed by the surgical guide instrument and system for ACL reconstruction and method in accordance with the invention.

The present invention includes a surgical system that allows surgeons to perform ACL reconstructions utilizing the principles of the relatively easier transtibial technique, while providing the improved graft positioning associated with the more technically difficult AM portal technique.

The surgical system in accordance with the invention is unique because it allows a guide wire to be directed from a path through the tibial ACL tunnel (the trans-tibial technique most familiar to practicing surgeons) to an anatomically correct position on the femur where the ACL normally attaches. While the AM portal technique (and its associated conventional instrumentation) is successful in anatomically positioning the guide wire on the femur, the steps required for doing so are much more difficult than passing the guide wire through the tibial tunnel.

Therefore, the present invention allows reliably anatomic femoral tunnel positioning with a traditional transtibial ACL reconstruction.

In one aspect of the invention, the surgical system includes a surgical guide instrument that is inserted external to the tibial tunnel through an arthroscopic portal.

In another aspect of the invention a method of ACL reconstruction is provided that resembles the transtibial technique with respect to technical ease, while providing an outcome with improved graft positioning resembling the more difficult AM portal technique.

In one aspect of the invention the surgical system includes a surgical guide instrument comprising an elongate member having a first end and a second end opposite the first end. The instrument includes a grippable handle section proximate the first end of the member, and a head section proximate the second end of the member. In one aspect of the invention, the head section has a groove formed therein, the groove including first and second ends. A protuberance extends into the groove intermediate the first and second ends of the groove, such that the groove has a varying width, in which the width proximate the protuberance is narrowed relative to the width of the groove proximate the first end.

According to another aspect of the invention, the handle section can be substantially cylindrical, and has a diameter that gradually decreases as the handle section extends from the first end of the member toward the second of the member.

According to another aspect of the invention, the handle section can be ergonomically contoured, and has a knurled surface for facilitating a user's grip of the instrument.

According to another aspect of the invention, the instrument includes an angled intermediate section between the handle section and the head section.

According to another aspect of the invention, the intermediate section can be bent at an angle of fifty to eighty degrees.

According to another aspect of the invention, the handle section and the intermediate section define a substantially cylindrical body having a diameter that is greatest where the handle section begins proximate the first end of the member, and gradually decreases until the intermediate section terminates at the head section.

According to another aspect of the invention, the head section includes an arcuate end portion defining the second end of the member.

According to another aspect of the invention, the width of the groove proximate the protuberance is less than the width of the groove proximate the first end and the second end.

According to another embodiment of the invention, a surgical system for use in performing anterior cruciate ligament reconstruction operations comprises an instrument having an elongate body section having a handle portion for a user to grasp the instrument. The handle portion is positioned proximate the proximal end of the instrument, and a head section is proximate the distal end of the instrument. The head section has a curvilinear groove formed therein adapted for receiving and frictionally engaging a guide wire.

According to another embodiment of the invention, the curvilinear groove includes first and second ends, and a protuberance extends into the groove intermediate the first and second ends of the groove for frictionally engaging the guide wire within the groove.

According to another embodiment of the invention, the groove has a varying width, and the width proximate the protuberance is narrowed relative to the width of the groove proximate the first end and the second end.

According to another embodiment of the invention, rotation of the instrument in a first direction increases frictional engagement of the wire within the groove, and rotation of the instrument in a second direction opposite the first direction releases the wire from frictional engagement within the groove.

According to another embodiment of the invention, the body section includes an intermediate portion positioned between the handle portion and the head section, and the intermediate portion is bent at an angle such that the instrument can be leveraged against a posterior cruciate ligament.

According to another embodiment of the invention, the body section can be substantially cylindrical, and has a diameter that gradually decreases as the body section extends from the first end of the instrument toward the head section.

According to another embodiment of the invention, the handle portion is contoured, and has a plurality of channels formed therein for facilitating the user's handling of the instrument.

According to another embodiment of the invention, the head section includes an end portion having a contour anatomically conforming to the femur.

According to another embodiment of the invention, the instrument can be made of a transparent material, so that the user can see the guide wire pass through the groove.

According to another embodiment of the invention, a method of performing an anterior cruciate ligament reconstruction on a human knee includes providing a surgical system. The surgical system includes an instrument having an elongate body section having a handle proximate a first end of the instrument, and a head section having a curvilinear groove formed therein and an arcuate end portion having a contour anatomically conforming to the femur. A guide wire is provided for ultimately guiding a graft through the tibia to a desired anatomic position on the femur, and inserting the guide wire through the tibia. The head section is inserted through a portal proximate the joint line between the tibia and the femur, and the guide wire is inserted into the head section groove. The instrument is rotated in a first direction to frictionally engage the guide wire within the head section groove, and the instrument can be moved to direct the guide wire to the desired anatomic position on the femur. The instrument may also be rotated in a second direction opposite to the first direction to release the guide wire from frictional engagement with the head section groove.

According to another embodiment of the invention, a surgical system for ACL reconstructions is provided. The system includes a surgical guide instrument, a guide wire and a guide wire sheath.

According to another aspect of the surgical system, the surgical guide instrument includes a head portion having a distal end that defines a phalange, a middle portion including a notch surface thereon and a proximal portion defining an elongate open-faced slot.

According to another aspect of the invention, the surgical guide instrument is inserted into the knee joint from outside the tibial tunnel, engaging with a transtibial guide wire (which is passed separately through the tibial tunnel) inside the joint to allow the guide wire and all subsequent femoral tunnel reaming and graft passage to be done exclusively through the tibial tunnel.

According to another aspect of the invention, the knee may remain at 90 degrees throughout femoral tunnel preparation.

According to another aspect of the invention the surgical system include a surgical guide instrument comprising an elongate member having a first end and a second opposing end. The instrument includes a grippable handle section defining the first end of the elongate member, and a head section comprising the second end of the elongate member. In one aspect of the invention, the head section includes a front-facing, open slot formed therein. The slot further includes a lip or stop member at the distal end thereof. The head section further includes a phalange offset by between 5-15 degrees from the longitudinal axis of the elongate member and a notch surface in the head section proximal to the phalange and distal to the open-facing slot. The orientation of the phalange and notch surface to each other is such that together they anatomically conform to the posterior aspect of the lateral femoral condyle and intercondylar notch wall, respectively. The orientation of the open slot is such that a guide wire can easily pass into the slot from the tibial tunnel, and—once then passing through the slot—will be directed to follow a path parallel with the plane defined by the phalange and simultaneously at an angle of roughly 45 degrees from the plane of the notch surface and 30 degrees offset from the long axis of the phalange. When the phalange and notch surface are pressed flush to the bony surface of the posterior lateral femoral condyle and intercondylar notch wall, the combined orientation of the phalange, notch surface and slot ensure an anatomic entrance point of the exiting guide wire into the femur, and further passage of the exiting guide wire safely in front of the posterior wall of the femur and along a trajectory that ensures adequate femoral tunnel length for later ACL reconstruction.

According to another aspect of the invention the surgical system includes a guide wire receivable by a guide wire sheath. The outer diameter of the guide wire sheath is less than an inner diameter of the open-facing slot so as to be receivable by the open-facing slot. The inner diameter of the guide wire sheath is greater than the outer diameter of the guide wire.

According to another aspect of the invention, a guide wire is deflected to an anatomically correct position on the surface of the lateral wall of the femoral intercondylar notch and then along an ideal trajectory through the distal femur, ensuring a safe and usable femoral tunnel.

BRIEF DESCRIPTION OF THE DRAWINGS

For a better understanding of the invention, and to show how the same may be carried into effect, reference will now be made, by way of example, to the accompanying drawings, in which:

FIG. 1A is an enlarged partial view of the instrument of FIG. 1.

FIG. 2A is an enlarged partial view of the instrument of FIG. 2.

FIG. 6 is another perspective view of the instrument of FIG. 1.

FIG. 6A is an enlarged partial view of the instrument of FIG. 6.

DETAILED DESCRIPTION OF THE INVENTION

Figure 1:
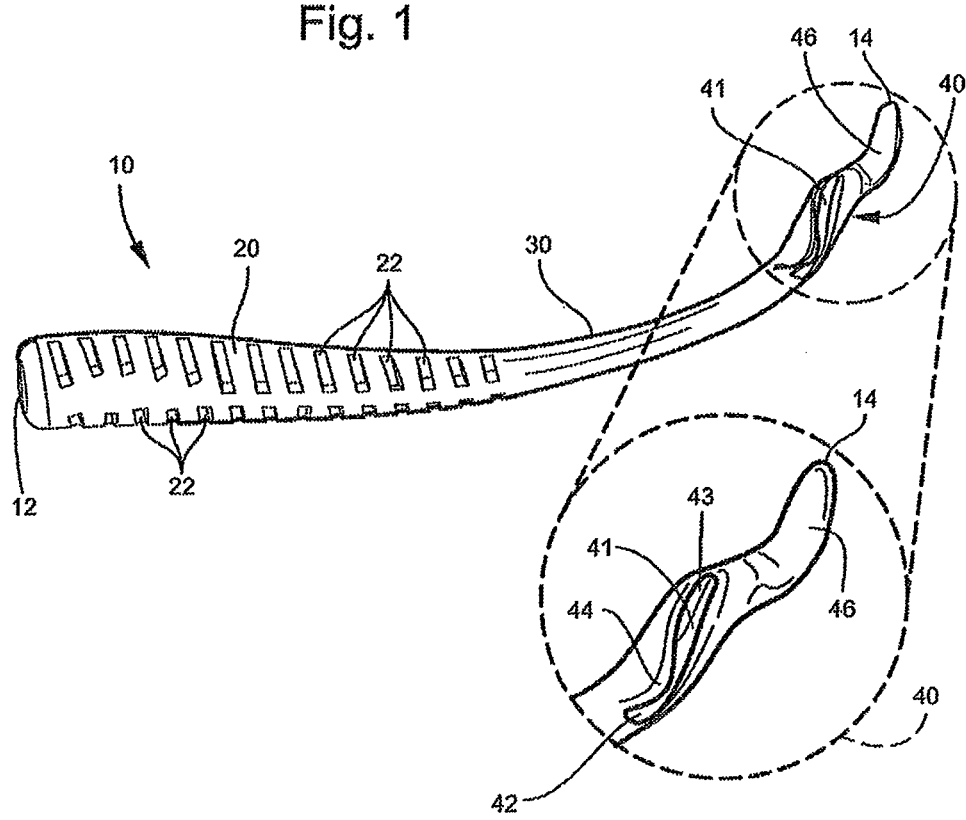
FIG. 1 is a perspective view of a surgical guide instrument according to a preferred embodiment of the invention.
Figure 2:
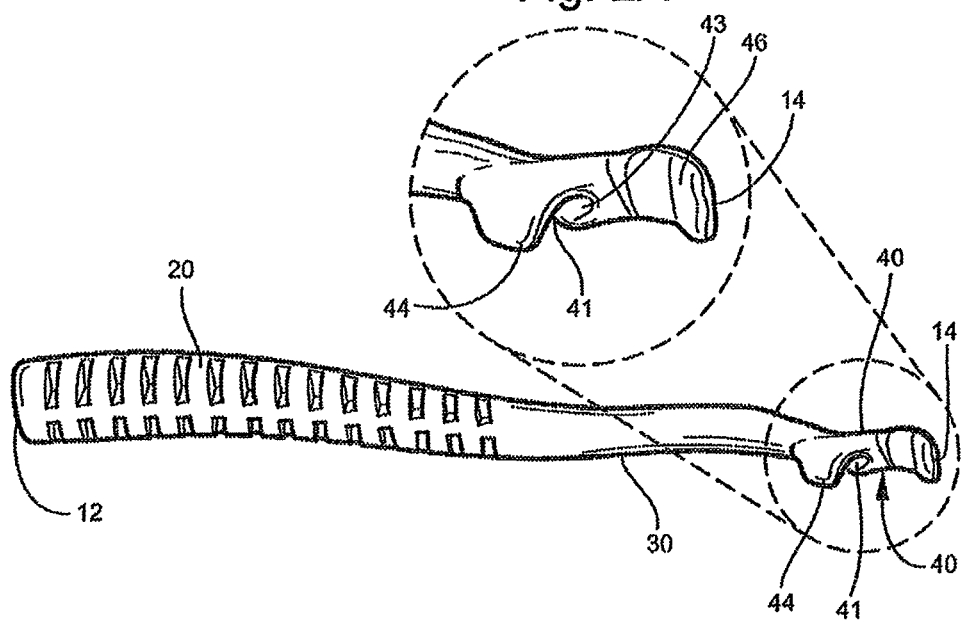
FIG. 2 is another perspective view of the instrument of FIG. 1.
Figure 3:
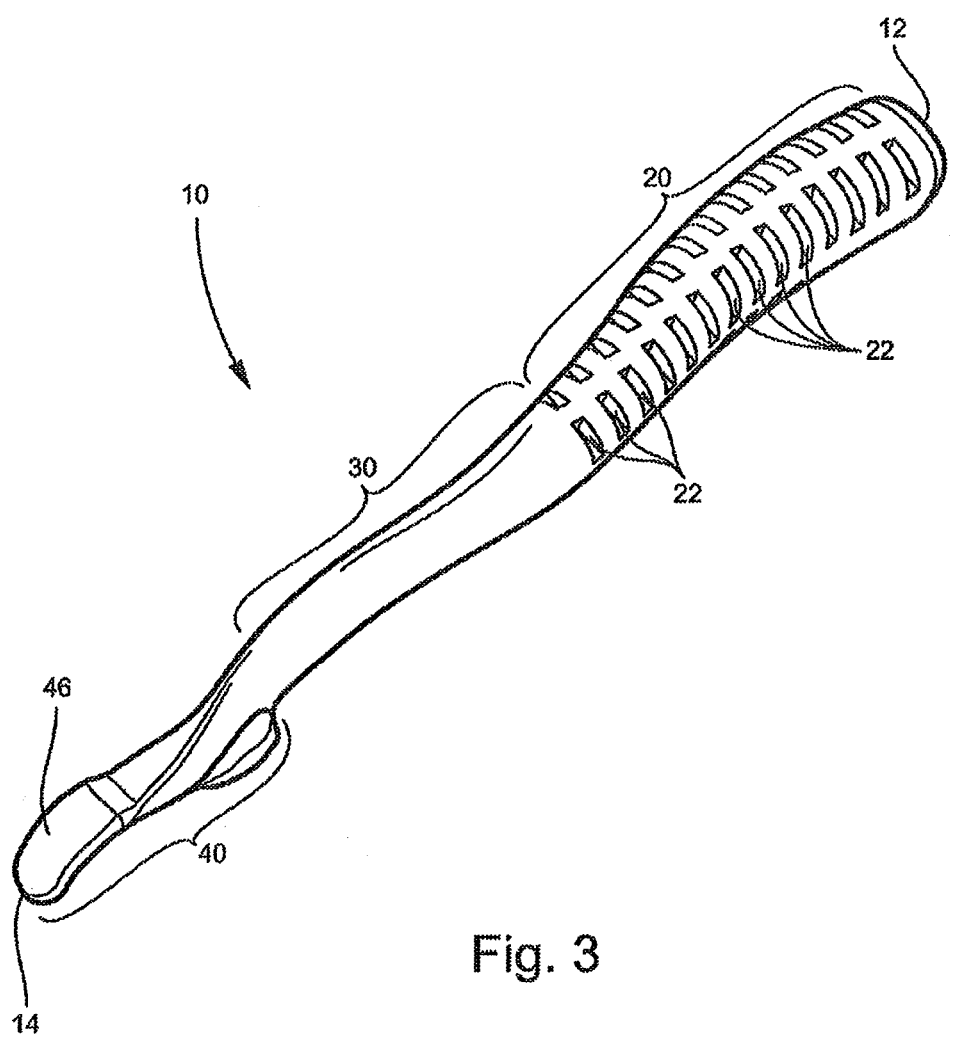
FIG. 3 is another perspective view of the instrument of FIG. 1.

A surgical guide instrument according to an exemplary aspect of the invention is illustrated in FIGS. 1-4, and shown generally at reference numeral 10. As shown in FIGS. 1-3, the surgical guide instrument 10 comprises an elongate member having a first proximal end 12, and a second distal end 14. The instrument 10 includes a grippable handle section 20 beginning at the proximal end 12, a head section 40 at the distal end 14, and an angled intermediate section 30 between the handle section 20 and the head section 40.

Figure 4A:
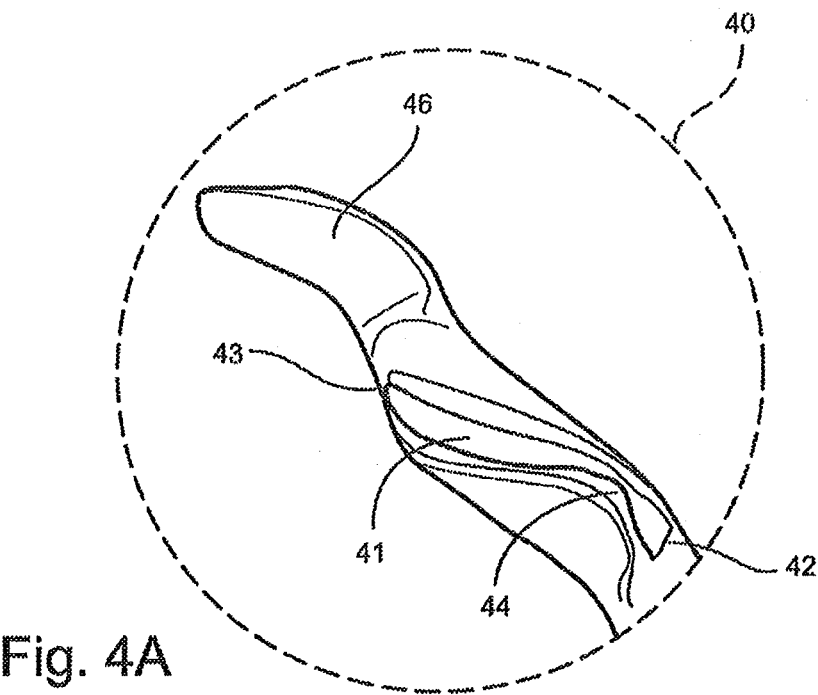
FIG. 4A is an enlarged partial view of the instrument of FIG. 4.
Figure 5A:
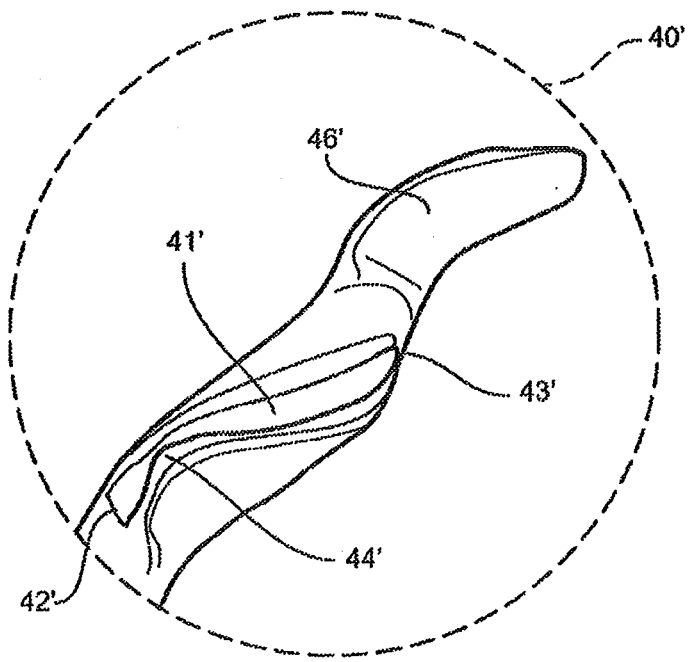
FIG. 5A is an enlarged partial view of the instrument of FIG. 5.

As shown in FIGS. 1A, 2A, 4A and 6A, the head section 40 has a curvilinear groove 41 formed therein having an entrance 42 and an exit 43. A protuberance 44 extends into the groove intermediate the first and second ends of the groove, whereby the groove has a varying width wherein the width proximate the protuberance is narrowed relative to the width of the groove at the entrance 42 and exit 43, as shown in FIGS. 1A, 4A, 6A. The head section 40 includes an arcuate end portion 46 located at the distal end 14 of the instrument 10, as shown in FIGS. 1A, 2A, 3 and 4A.

Figures 4, 5:
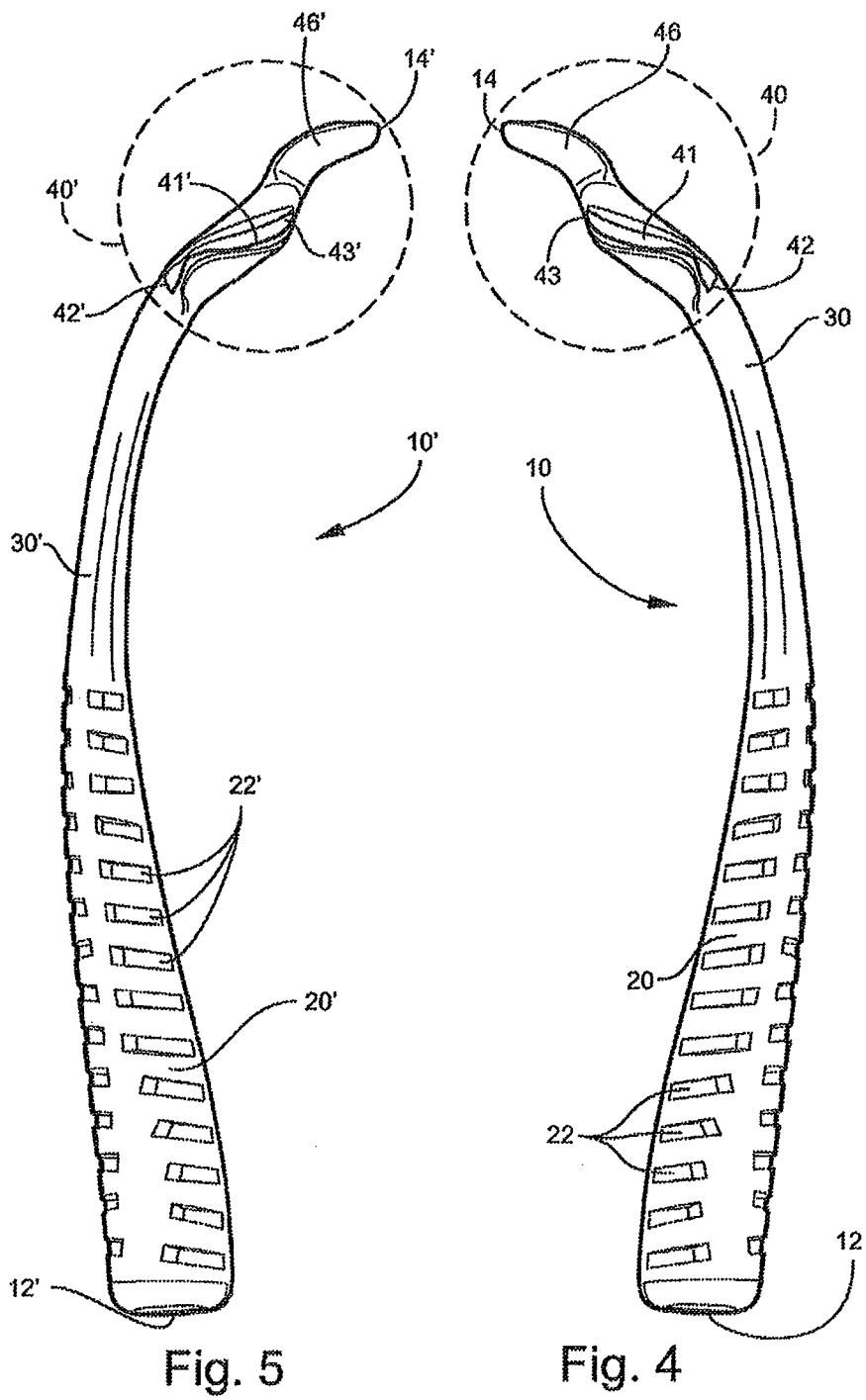
FIG. 4 is another perspective view of the instrument of FIG. 1.
FIG. 5 is a perspective view of a surgical guide instrument, according to another preferred embodiment of the invention.

The handle 20 can be contoured, as shown in FIGS. 1-4, for ergonomic hold by the user. Also, the handle section 20 can have a knurled surface for facilitating ergonomic hold by the user. As shown in FIGS. 1, 3 and 4, the knurled surface can be comprised of a series of channels 22 formed in the handle section 20.

The intermediate section 30 can be bent at an angle, as shown in FIGS. 1 and 4. Preferably, the intermediate section 30 is bent at an angle of about fifty to eighty degrees.

The handle section 20 and intermediate section 30 define a generally cylindrical member having a diameter that is greatest where the handle section 20 begins at the proximal end 12 of the instrument 10, and gradually decreases until the intermediate section 30 terminates at the beginning of the head section 40, as shown in FIG. 3.

The instrument 10 can be used in performing surgery on the human knee, in particular, anterior cruciate ligament (ACL) reconstruction. As such, different versions for use on left and right knees are provided. The instrument 10, illustrated in FIGS. 1-4, is a left knee version. An instrument for use in operating on right knees, according to a preferred embodiment of the invention, is illustrated in FIG. 5, and shown generally at reference numeral 10'. The right knee version 10' can be a mirror image of the left knee version 10, as illustrated in FIGS. 4, 4A, 5, and 5A. The instrument 10' can be otherwise identical in structure to instrument 10.

A method of using the instrument 10, according to a preferred embodiment of the invention, is illustrated in FIGS. 7-11. As shown in FIGS. 7-11, the instrument 10 can be used to perform a transtibial technique anterior cruciate ligament (ACL) reconstruction procedure. It should be noted that the Figures illustrate a method of using the instrument 10 in a left knee ACL reconstruction.

Figure 7:
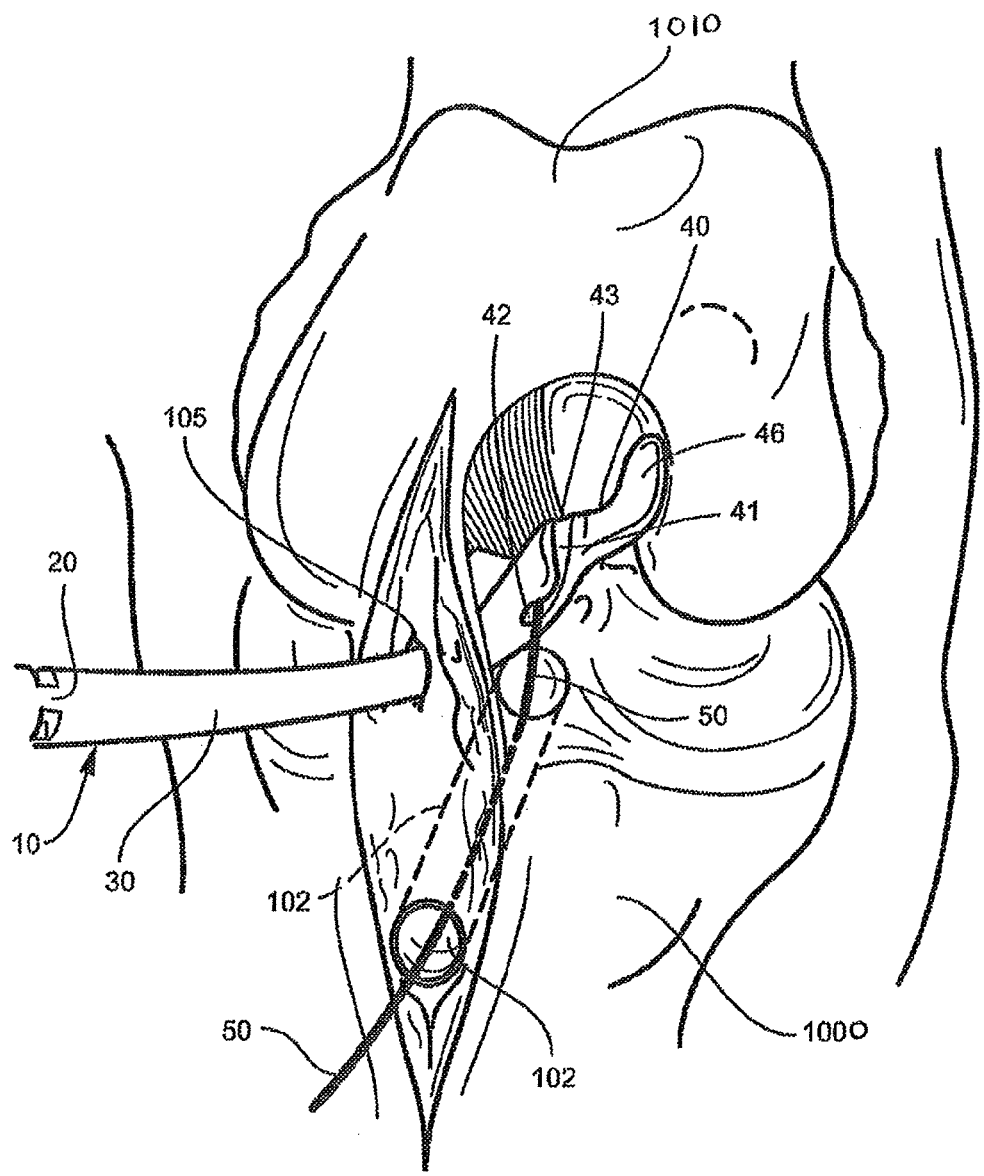
FIG. 7 is an environmental perspective view illustrating a method of using the instrument of FIG. 1, according to a preferred embodiment of the invention.
Figure 7A:
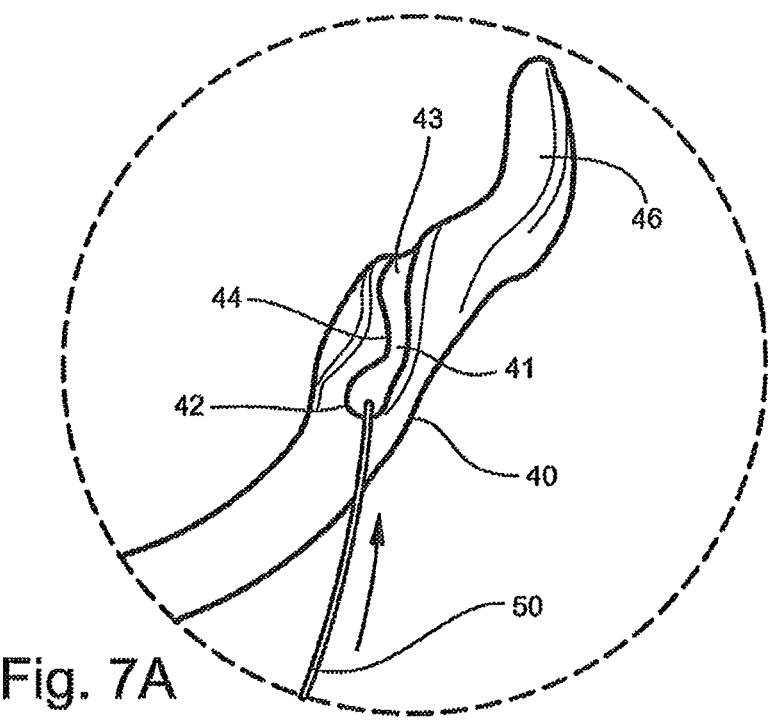
FIG. 7A is an enlarged partial schematic view of the instrument in FIG. 7.

A bone tunnel 102 is drilled through the tibia bone 100 such that the tunnel 102 enters the knee joint where the ACL would normally attach. A small incision is made at the joint line of the tibia 100 and femur 1010, creating an anteromedial (AM) portal 105. As shown in FIG. 7, the distal end 14 of the instrument 10 is inserted through the AM portal 105. A guide wire 50 is passed through the transtibial tunnel 102, and inserted into the entrance 42 of the groove 41 of the head section 40, as shown in FIGS. 7 and 7A. The term "guide wire" as used herein refers generally to any elongate member, such as a wire or pin, that can be used in an ACL reconstruction to guide a cannulated drill and/or an ACL graft through the tibial tunnel 102 to an anatomic position on the femur 1010.

Figure 9A:
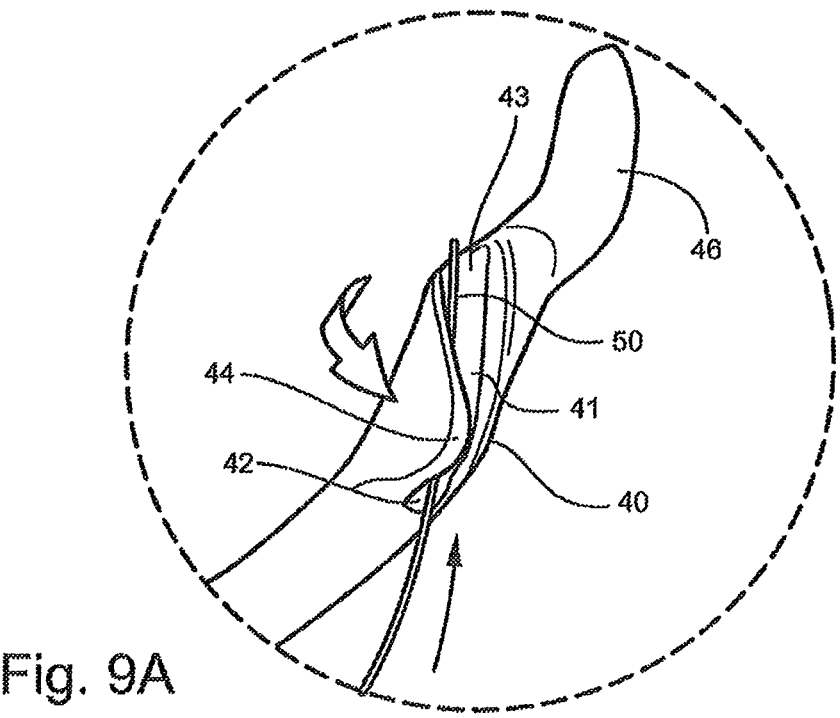
FIG. 9A is an enlarged partial schematic view of the instrument in FIG. 9.
Figure 8:
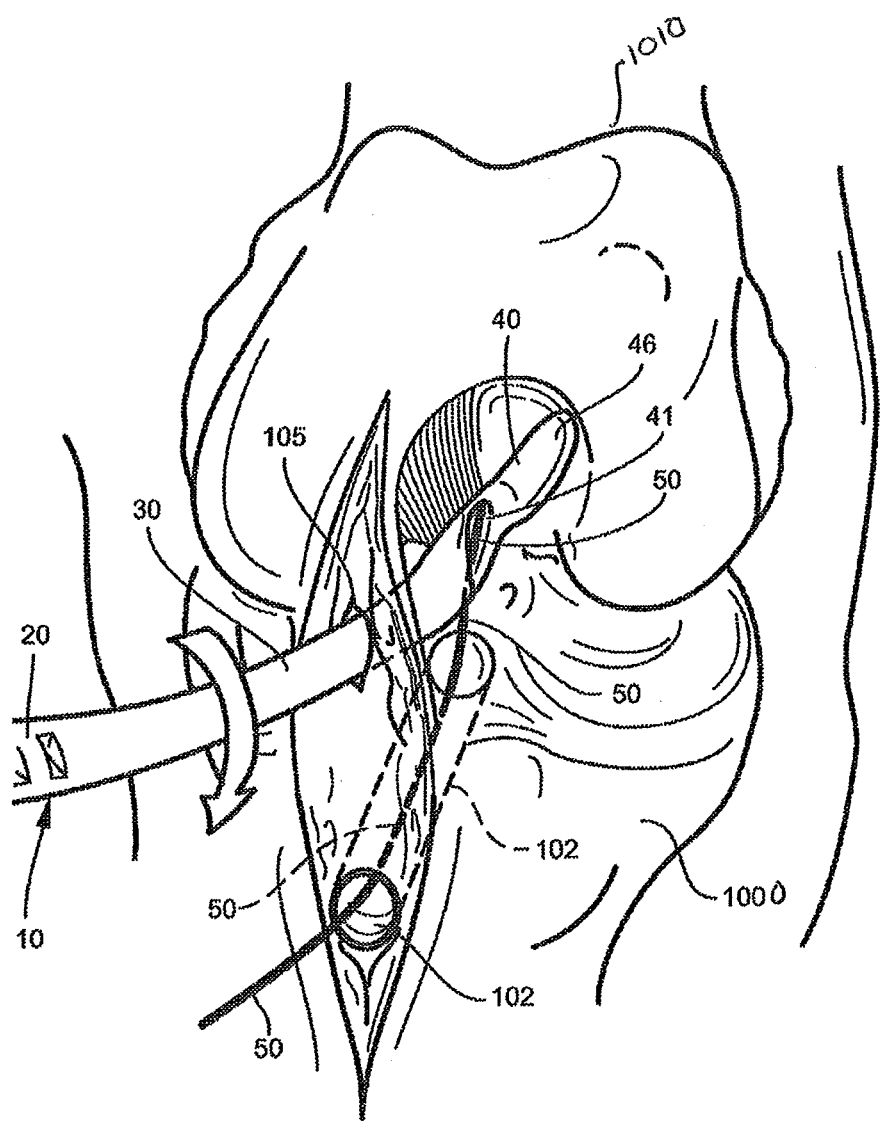
FIG. 8 is another environmental perspective view illustrating a method of using the instrument of FIG. 1, according to an embodiment of the invention.
Figure 9:
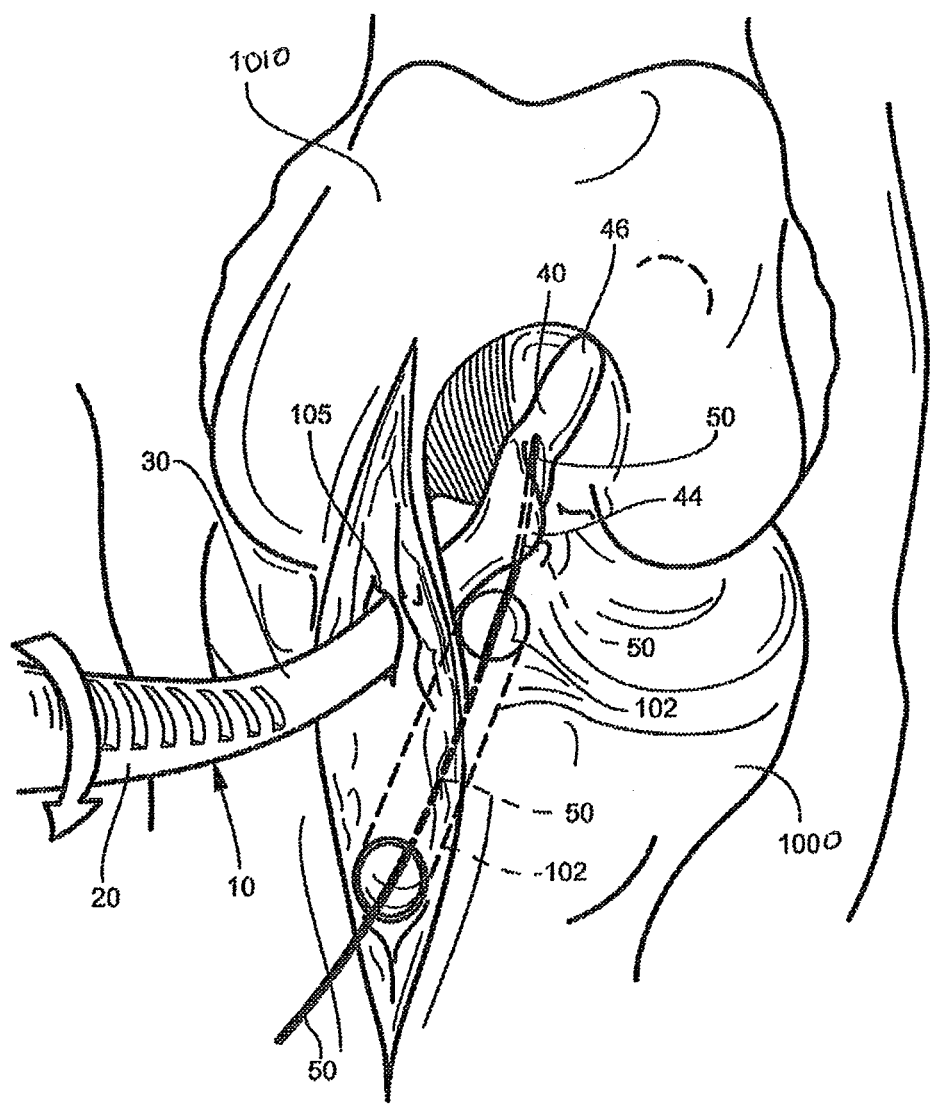
FIG. 9 is another environmental perspective view illustrating a method of using the instrument of FIG. 1, according to an embodiment of the invention.

The guide wire 50 is inserted into the groove 41, and the instrument 10 is rotated clockwise, as shown in FIG. 8, to capture the wire within the groove 41. As the instrument 10 is rotated clockwise, the protuberance 44 in the groove 41 engages the guide wire 50. Further clockwise rotation rotation of the instrument 10 increases the frictional engagement. As shown in FIGS. 9 and 9A, the instrument is rotated inwardly toward the wire 50 until the protuberance 44 engages the wire 50 such that it is securely held within the groove 40 of the head section.

Figure 10:
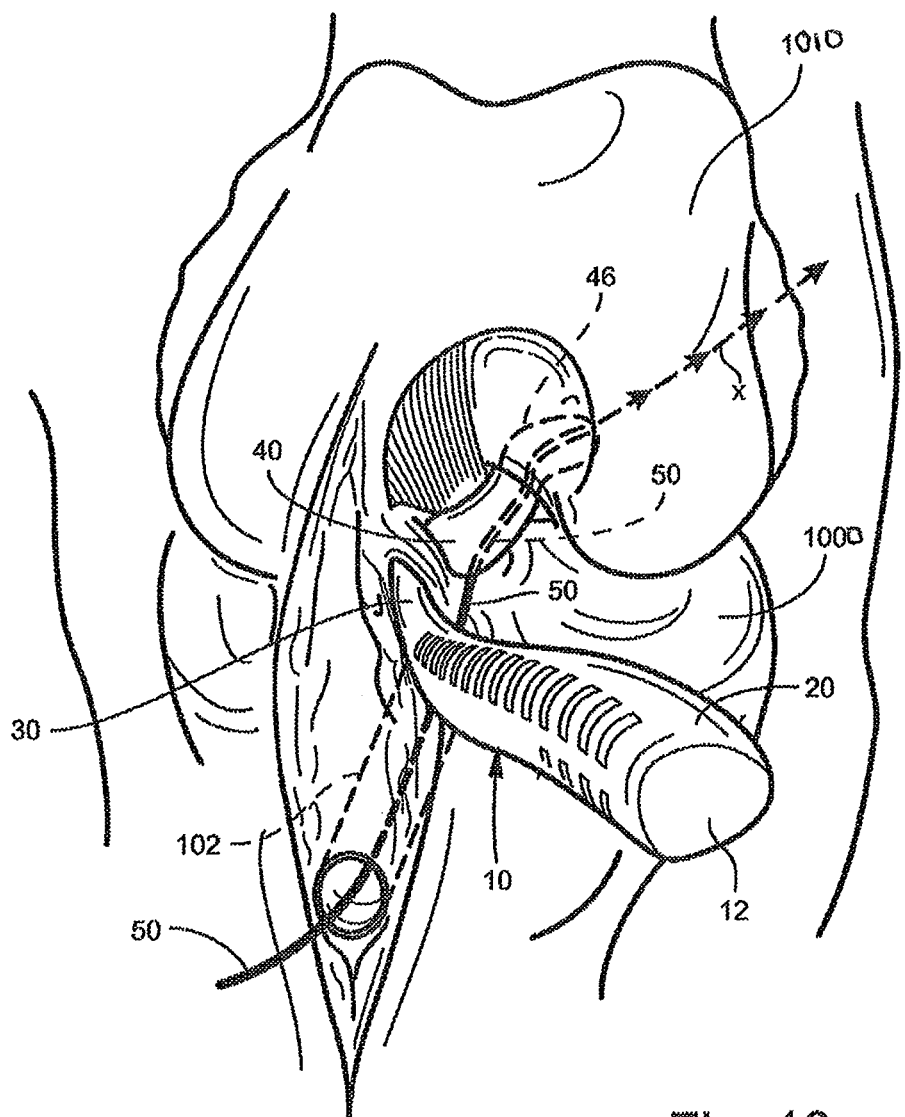
FIG. 10 is another environmental perspective view illustrating a method of using the instrument of FIG. 1, according to an embodiment of the invention.

With the wire 50 securely held within the groove 41, the instrument 10 is moved to be directly apposed to the femur 1010, and the arcuate end portion 46 is hooked around the femur 1010, as shown in FIG. 10. The anatomic contouring of the end portion 46, in combination with the curvilinear orientation of the interior of the groove 41, directs the wire 50 to a desired anatomic position on the femur 1010. The end portion 46 of the head section 40 anatomically conforms to the normal bony contour of the femur 1010. When apposed to the femur 1010, the contour of the end portion 46 positions the exit 43 of the head section groove 41 at the center of the ACL's normal attachment. Broken arrows designated with reference letter X, illustrates the trajectory of the guide wire 50. The wire 50 is guided by the instrument 10 to the proper anatomic position on the femur 1010, as the wire is drilled into the femur 1010 through the femoral tunnel 112.

Figure 11:
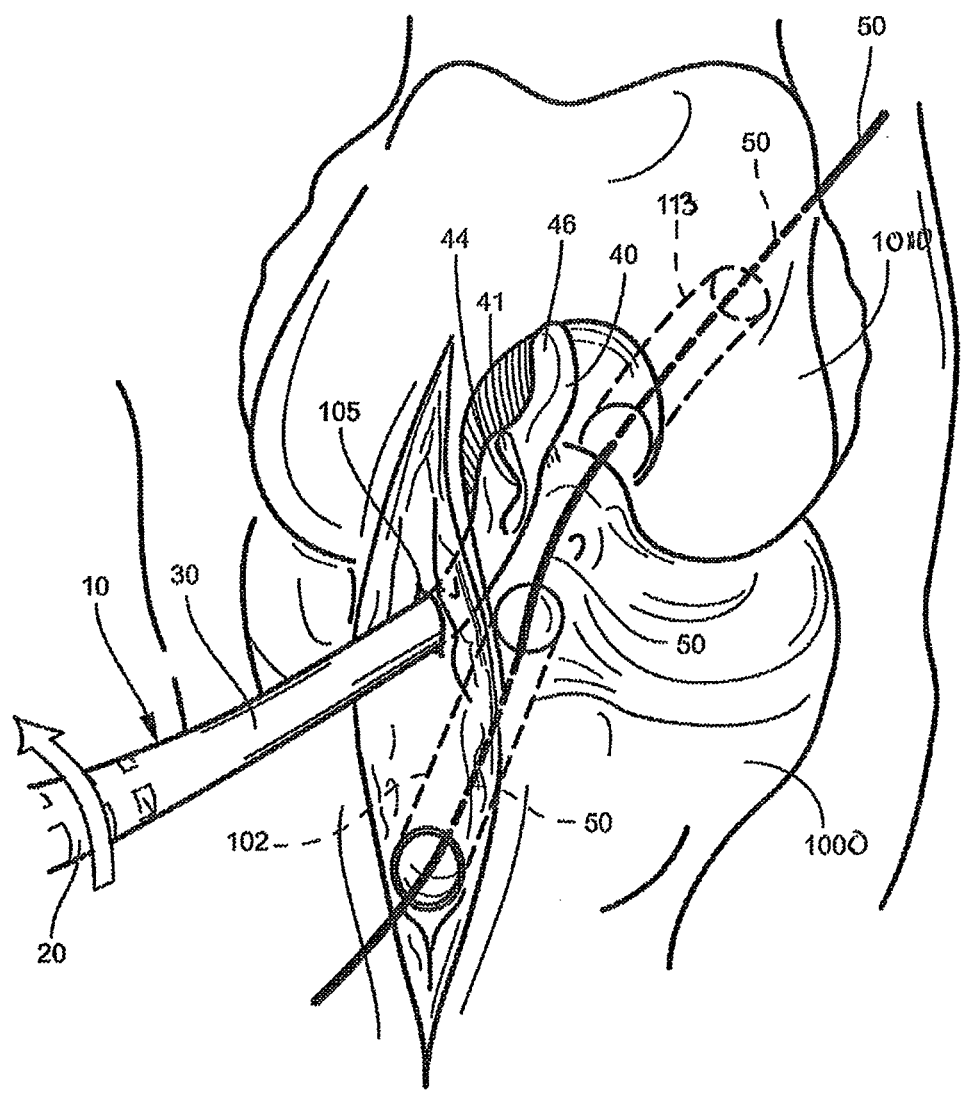
FIG. 11 is another environmental perspective view illustrating a method of using the instrument of FIG. 1, according to an embodiment of the invention.

When the wire 50 has been drilled into and positioned anatomically on the femur 1010, the instrument 10 is rotated counterclockwise, thereby disengaging the wire 50 from the groove 41, as shown in FIG. 11. The curvilinear groove 41 in the head section 40 provides just enough constraint to allow appropriate direction of the guide wire 50, while also being flexible enough to allow the instrument 10 to be removed from the wire 50 after the wire 50 has been drilled into position on the femur 1010.

The instrument 10 is removed, and the guide wire 50 can be used to pull the ACL graft through the tibial tunnel 102 and femoral tunnel 113 for attachment to the anatomic position on the femur 1010. The remainder of the operation can proceed identically to a conventional transtibial ACL reconstruction. Hyper flexion of the knee is not required, as in conventional AM Portal ACL reconstruction, thereby improving visualization for the surgeon and speed of the operation. In addition, the ultimate result is a graft positioned in a more effective and anatomic fashion.

As noted above, FIGS. 7-11 illustrate the use of the instrument 10 in a left knee ACL reconstruction. The right knee version 10' can be used in a right knee ACL reconstruction, utilizing the same method described above, except that the instrument 10' is rotated counterclockwise to engage the guide wire, and rotated clockwise to disengage the guide wire from the instrument 10'.

Because the groove 41 of the head 40 is open, the instrument 10 can be inserted from a location separate from the guide wire 50. This allows the instrument 10 to apply a directive force to the wire 50 without being influenced by the tibial tunnel 102. In contrast, prior art instruments for ACL reconstruction typically have a "closed" construction that requires that they be passed along the same path that the guide wire takes.

The curvilinear groove 41 and overhanging protuberance 44 of the head 40 provide an element of constraint to the wire 50 when the instrument 10 is rotated inwardly. After the wire 50 is engaged in the groove 41, the instrument 10 can be used to direct the wire 50 where the surgeon wants it to go.

The end portion 46 of the head 40 conforms to the bony contour of the femur 1010. The orientation of the interior of the groove 41 relative to the end portion 46 directs the guide wire 50 in a specific trajectory that avoids the back of the femur 1010, and exits the femur 1010 in a safe location. This specific trajectory results in a sufficiently long and intact bone tunnel.

The bend in the intermediate section 30 of the instrument 10 allows the instrument to be levered against the posterior cruciate ligament (PCL), the ligament directly adjacent to the ACL, both protecting the PCL and providing additional stability to the relationship of the groove 41 and end portion 46 of the head 40 with the femur 1010. It also allows the surgeon to see the passage of the wire 50 from the tibial tunnel 102 into the groove 41 of the instrument 10. In the event that the surgeon decides to pass the wire 50 into the instrument 10 from a separate location, i.e. an accessory central portal, this allows for the surgeon's visualization of the passage of the wire 50.

The gripped and contoured handle 20 provide for ergonomic hold by the surgeon, optimizing leverage in providing additional stability to the instrument 10 as the wire 50 is passed therethrough.

The instrument can be made of stainless steel, a medical grade plastic such as polycarbonate-ISO or other suitable material. Preferably, the instrument 10 is made from a medical grade transparent plastic. As such, the instrument 10 is transparent, thereby allowing for visualization of the wire 50 as it passes through the groove 41 during drilling. The transparent instrument 10 can include opaque guide markings to assist the surgeon with placement of the device on the femur 1010.

Referring now to FIGS. 12-15 an alternate exemplary embodiment of a surgical guide instrument and system for ACL reconstructions is depicted. The surgical system 100 broadly includes a surgical guide instrument 110, a guide wire 170 and a guide wire sheath 180. Those of skill in the art will appreciate, however, that surgical guide instrument 110 may be used as a stand-alone instrument as opposed to being used solely in a surgical system and both embodiments are contemplated herein.

Surgical instrument 110 comprises an elongate member 111 having a first proximal end 112, and a second distal end 114. The instrument 110 includes a grippable handle section 120 beginning at the proximal end 112, a head section 140 at the distal end 114, and an angled intermediate section 130 between the handle section 120 and the head section 140.

As with the first embodiment, the instrument in accordance with the alternate embodiment may be made of stainless steel, a medical grade plastic such as polycarbonate-ISO or other suitable material. As those of skill in the art will appreciate, the instrument 110 may also be constructed from a medical grade, biocompatible, transparent plastic to allow visualization by the surgeon of the wire 170 as it passes through open-faced slot 141 (hereinafter described) during drilling. The transparent instrument 110 may include opaque guide markings to assist the surgeon with placement of the device on the femur 1010.

Figure 12:
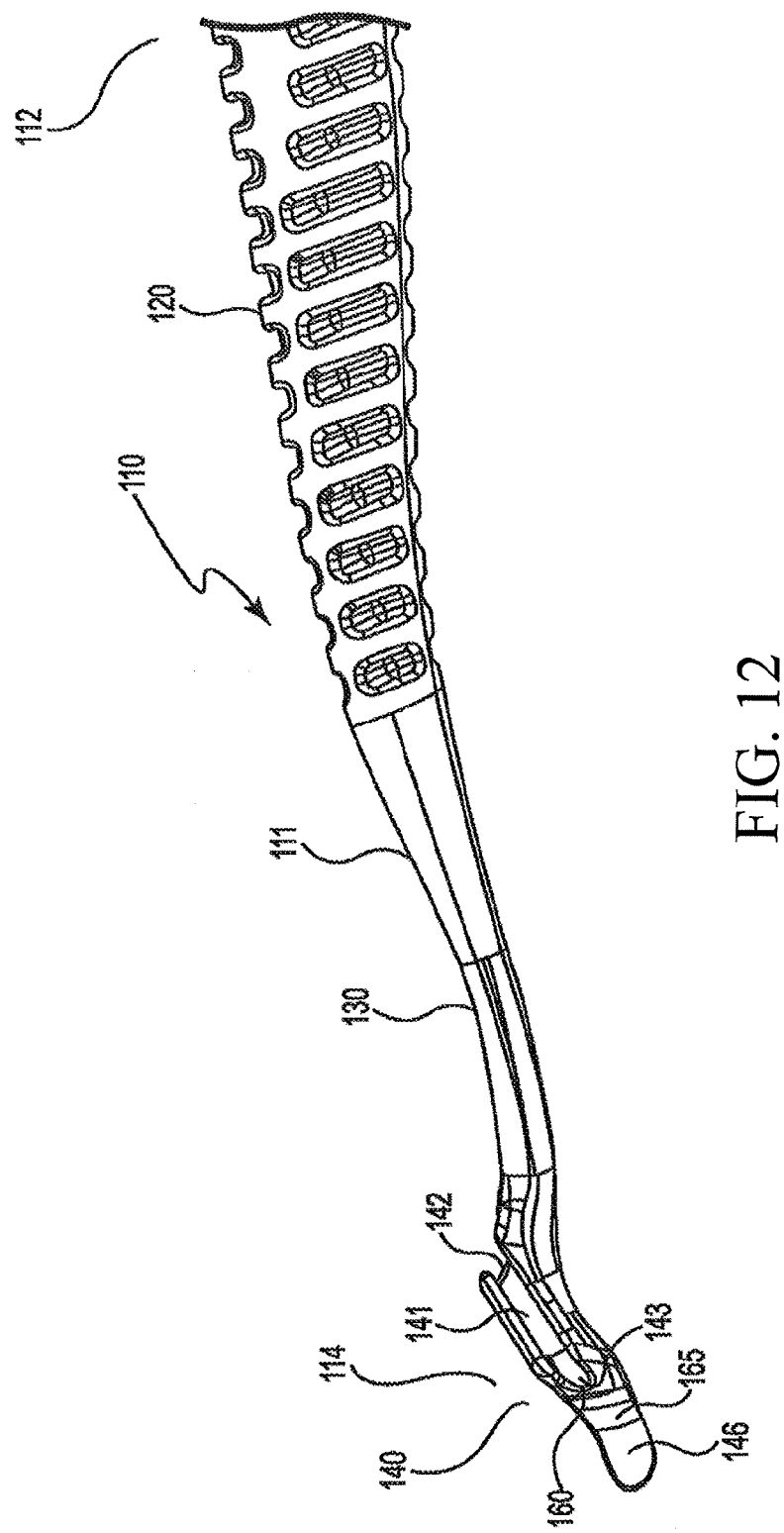
FIG. 12 is a perspective view of an embodiment of the surgical guide instrument in accordance with the invention.
Figure 13:
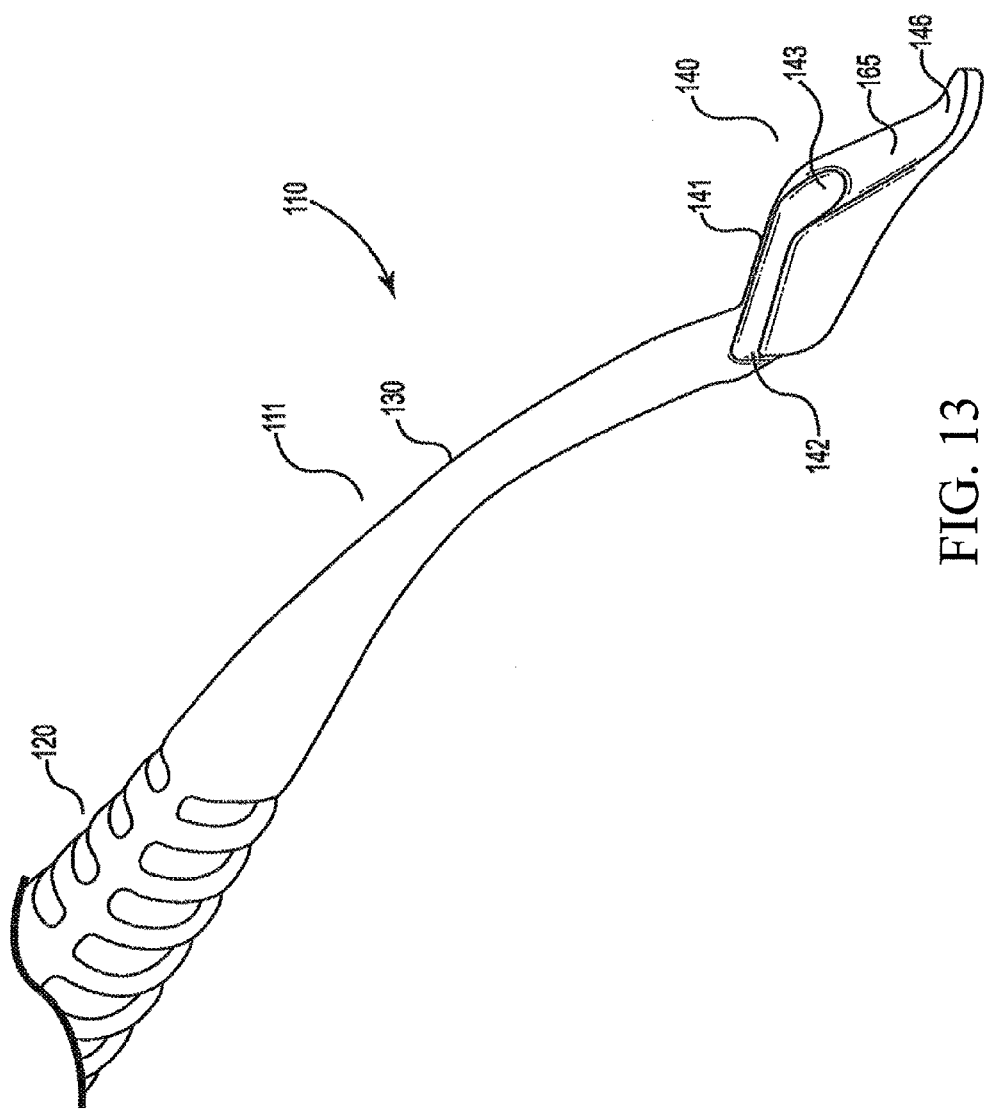
FIG. 13 is an enlarged perspective view of the surgical guide instrument of FIG. 12.
Figure 14:
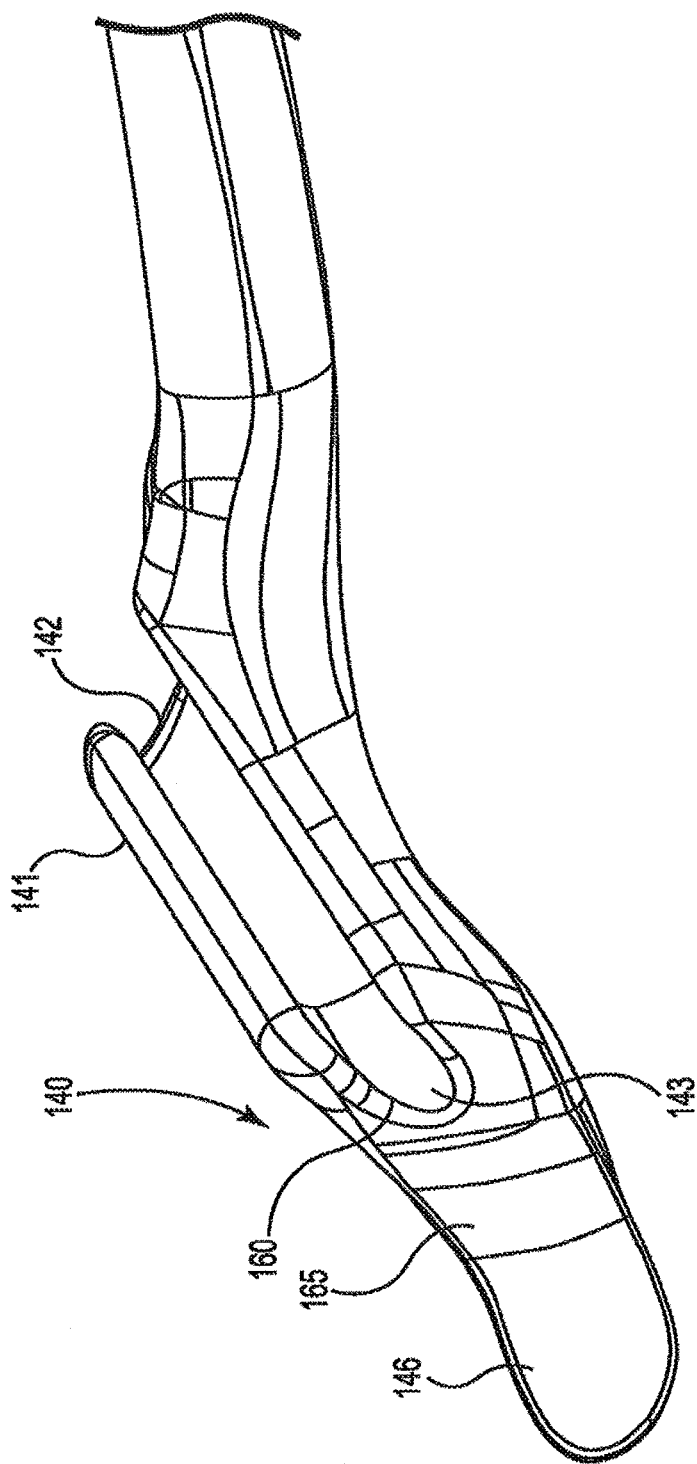
FIG. 14 is an enlarged view of the distal portion of the surgical guide instrument of FIG. 12.

As best seen in FIGS. 12-14, the head section 140 includes a substantially straight open-faced slot 141 formed therein having an entrance 142 and an exit 143. The head section 140 includes a phalange 146 located at the distal end 114 of the instrument 110. The tip of phalange 146 is rounded to protect damage to tissue with which it will come into contact. As best seen in FIGS. 12 and 14, phalange 146 is contoured and offset from the longitudinal axis of the elongate member at an angle of from 5 degrees to about 15 degrees to facilitate engagement with the femur. The contour of the phalange 146 anatomically conforms to the normal bony contour of the femur 1010. When apposed to the femur 1010, the contour of the end portion 46 positions the exit 143 of the head section groove 141 at the center of the ACL's normal attachment. The guidewire 170 is thus guided by the surgical guide instrument 110 to the proper anatomic position on the femur 1010, as the wire is drilled into the femur 1010 through the femoral tunnel 102. One advantage of the present invention is that, during an ACL procedure, the slot allows the surgeon to visualize both the natural attachment point and the attachment point that the surgical instrument in accordance with the invention identifies. A majority of the time the two attachment points correspond; however, if they do not, the surgeon has the ability to make adjustments as needed to ensure that the two points do correspond.

Exit 143 of phalange 146 includes a lip or stop member 160. Stop member 160 is raised in height by approximately 1 mm. In operation, stop member 160 prevents sheath 180 from advancing out of exit 143.

Head section 140 also includes a notch surface 165. The notch surface 165 does not include a notch or groove but rather is named "notch surface" because it is contoured to fit the anatomic contour of the femoral intercondylar notch. The function of this surface on the device is designed to contour to the normal anatomy of the femur in that area. When the distal phalange and the notch surface are both placed up against their respective surfaces within the knee joint, their orientation with respect to the slot directs the guide wire appropriately. Those of skill in the art will appreciate the head section 140 does not necessarily need to have a surface that conforms to the intercondylar notch so long as the surgeon has the ability to manually position the wire drill, twist it with the surgical instrument to position the wire drill at the desired impact point on the femoral head and hold it there while drilling.

The handle 120 may be contoured, as shown in FIGS. 12-13, for ergonomic hold by the user. Also, the handle 120 can have a knurled surface for facilitating ergonomic hold by the user. The knurled surface may be of any construction or configuration known to those of skill in the art so long as it presents an effective hand-graspable surface.

The intermediate section 130 of the elongate member 111 may be bent at an angle of from about fifty to eighty degrees, as shown in FIGS. 12-13, offset from a longitudinal axis of the elongate member 110. The bend in the intermediate section 130 of the elongate member 111 allows the surgical guide instrument to be levered against the posterior cruciate ligament (PCL), the ligament directly adjacent to the ACL, both protecting the PCL and providing additional stability to the relationship of the slot 141 and phalange 146 with the femur 1010. It also allows the surgeon to visualize the passage of the guide wire 170 and sheath 180 from the tibial tunnel 102 into the slot 141.

The handle section 120 and intermediate section 130 define a generally cylindrical member having a diameter that is greatest where the handle section 120 begins at the proximal end 12 of the instrument 110, and gradually decreases until the intermediate section 30 terminates at the beginning of the head section 140, as shown in FIGS. 12-13.

Those of skill in the art will appreciate that modifications can be made to the surgical instrument. For example, the instrument does not necessarily need to be integrally made but rather could be modular. The handle section 120 and the intermediate section could be separate pieces or could form one piece. Additionally, the head section 140 may be manufactured as a separate piece. The pieces (two or three, as described) would slidingly fit together in a friction fit.

Figure 15B:
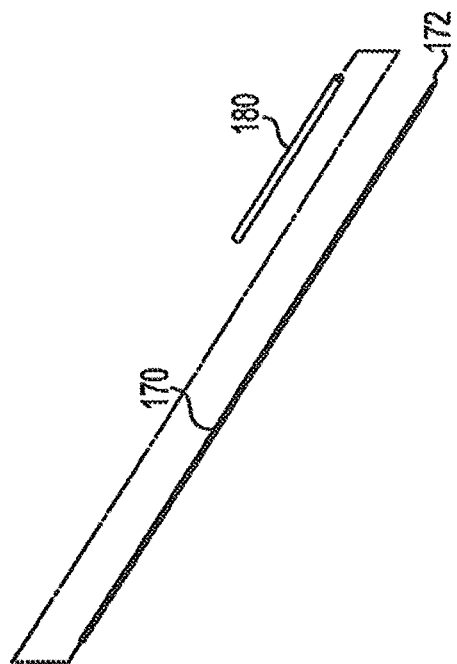
FIG. 15B is a perspective view of the assembly of the guide wire and sheath in accordance with the invention.
Figure 15A:
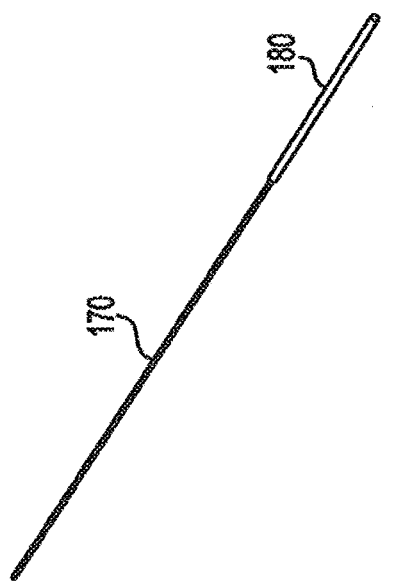
FIG. 15A is a perspective view of the guide wire and sheath in accordance with the invention.

Referring now to FIGS. 15A and 15B, guidewire 170 and sheath 180 comprise the second two elements of the surgical system in accordance with the invention. Guide wire 170 may be a thin, flexible wire generally known to those of skill in the art that can be inserted into the anatomical space and which is used to guide the placement of the ACL graft as will hereinafter be explained in detail.

Guide wire sheath 180 is a generally cylindrical tube defining a guide wire lumen therewithin. Guide wire sheath 180 is structured to have an inner diameter that will accommodate the outer diameter of guide wire 170. The outer diameter of guide wire sheath 180 is less than the inner diameter of open-face slot 142 to ensure that guide wire sheath 180 is easily received therewithin. The outer diameter of guide wire sheath 180 is structured to be less than the height of stop member 160 such that stop member 160 prevents guide wire sheath 180 from exiting the exit 143 of open-faced slot 141.

Guide wire sheath 180 need not be an annular tube over the guide wire 170. Rather those of skill in the art will appreciate that a molded piece that includes small finger holds on the proximal end could also be used so long as the surgeon can pull it out without using a hemostat. An alternative embodiment may be one which is designed to split when removed so that it can be removed without having the de-chuck the drill. An alternative embodiment may also include a device that combines with the reamer so that the drill is inserted first and the reamer follows thus eliminating the need to change tools.

In operation, the surgical guide instrument and surgical system in accordance with the alternative embodiment of the invention will now be described.

Insertion:

Following preparation of the tibial tunnel 102, the corresponding right or left surgical guide instrument 110 (7 mm or 5.5 mm notch surface length), depending on surgeon preference and planned femoral tunnel 113 diameter) is inserted through the standard medial portal. The surgical guide instrument 110 is advanced under arthroscopic visualization into the intercondylar notch such that the entrance 142 of slot 141 is positioned above the intraarticular aperture of the tibial tunnel 102.

Wire/Sheath 180 Assembly:

The sheath 180 and flexible guide wire 170 are assembled by advancing the sheath 180 to the end of the sharp tip of the wire 170. Ideally the end of the sheath 180 will be flush with the sharp distal tip 172 of the flexible guide wire 170.

Wire/Sheath 180 Insertion:

The sheath 180 and flexible guide wire 170 are then grasped together at the base of the sheath and advanced together by hand through the tibial 102 tunnel. Insertion in this manner prevents the sheath 180 from advancing past the distal sharp tip 172 of the flexible guide wire 170, and vice versa. Under direct arthroscopic visualization, the end of the wire/sheath combination is directed into the joint space, and then into the entrance 142 of slot 141 of the surgical guide instrument 110, in accordance with the invention. Gentle tipping of the surgical guide instrument 110- or slight extension of the knee—may improve alignment of the slot 141 with the trajectory of the flexible guide wire 170 and sheath 180, making their insertion easier. After engaged within the entrance of the slot 141, the flexible guide wire 170 and sheath 180 are advanced until the sheath 180 is seated against the stop member 160 at the distal end of the slot 141. The surgical guide instrument 110 and now-seated wire 170—sheath 180 combination are then advanced as a unit into the intercondylar notch, effectively deflecting the course of the flexible guide wire 170 along a more anatomic trajectory.

Seating:

After the flexible guide wire 170, sheath 180 and surgical guide instrument 110 are appropriately engaged (as above), they are advanced together into the posterior aspect of the intercondylar notch, the distal phalange 146 of the surgical guide instrument 110 hooking around the posterior wall of the lateral femoral condyle. A gentle anterior translatory force may be applied to the surgical guide instrument 110 to confirm capture of the phalange 110 on the back of the femur. After the distal phalange 146 is positioned, the notch surface 165 is pressed flush against the wall of the intercondylar notch. The path of the flexible guide wire 170 may now be anticipated based on the visualized distal end 143 of slot 141, the height of this path relative to the roof of the notch 165 adjusted based on surgeon preference. To help guide the appropriate positioning of this wire exit point, the center of the femoral insertion can be marked with a curette prior to seating of the surgical guide instrument.

Drilling:

After the surgical guide instrument 110 is positioned as above, the sharp distal end 172 of flexible guide wire 170 is drilled into the femur 1010 from outside the tibial tunnel 102 using a motorized drill known to those of skill in the art. The flexible guide wire 170 is advanced through the sheath 180 and into the femur, exiting the soft tissues of the distal thigh. The cutaneous wire exit point should be confirmed as being in the anterior half of the lateral thigh to assure integrity of the posterior wall of the femoral tunnel during subsequent reaming.

Surgical Guide Instrument Extrication:

After the position and trajectory of the flexible guide wire 170 are deemed anatomically acceptable, the sheath 180 is withdrawn antegrade from the guide wire 170 using a hemostat from outside the tibial tunnel 102. Removal of the sheath 180 allows the surgical guide instrument 110 to be separated from the flexible guide wire 170 by increasing the space available for the wire within the surgical guide instrument 110 slot. After the sheath 180 is removed, the surgical guide instrument 110 can be pushed posteriorly such that the guide wire passes through the open portion of the slot. After the surgical guide instrument 110 is translated past the flexible guide wire 170 in this way, it can be internally rotated and removed from the knee via the medial portal. The position of the flexible guide wire 170 can then be scrutinized and—if necessary—removed and repositioned. If acceptably positioned through the center of the femoral insertion, the surgeon may proceed with reaming of the femoral tunnel 113.

Reaming:

After the position of the flexible guide wire 170 is deemed acceptable, a cannulated, flexible or low-profile reamer, known to those of skill in the art, is passed through the tibial tunnel 102 and over the flexible guide wire 170 to ream the femoral tunnel. If there is uncertainty about the thickness of the posterior wall of the femoral tunnel 113, an initial 1-2 mm impression can be reamed onto the intercondylar wall—with the reamer then temporarily withdrawn—to confirm integrity of the posterior wall. If the tunnel aperture is deemed appropriate in position and size, the femoral tunnel reaming may be completed and the reamer withdrawn from the knee.

Completion of ACL Reconstruction:

Subsequent graft passage and graft fixation are performed as per standard transtibial ACL reconstruction known to those of skill in the art.

A surgical guide instrument, a surgical system and their methods of use are described herein. Various changes can be made to the invention without departing from its scope. The above detailed description of the invention are provided for the purpose of illustration only and not limitation; the invention being defined by the following claims and equivalents thereof.

What is claimed is:

1. A system for use in ACL reconstruction comprising:
a surgical guide instrument including an elongate member having first and second ends, a hand-graspable handle proximate the first end of the elongate member, and a head portion proximate the second end of the elongate member, the head portion including a curved phalange formed at a distal end of the head and an open-faced slot formed at a proximal end of the head, the slot including a guide wire entrance and a guide wire exit, the guide wire exit further including a stop member thereon, said phalange including a notch surface thereon structured to engage the femoral intercondylar notch;
a guide wire structured to be slidingly receivable in said open-faced slot; and
a guide wire sheath structured to be positioned over said guide wire and adjacent said stop member.

2. The system according to claim 1, wherein the hand-graspable handle is substantially cylindrical, and has a diameter that gradually decreases as the handle section extends from the first end of the member toward the second of the member.

3. The system according to claim 1, wherein the hand-graspable handle is ergonomically contoured, and has a knurled surface for facilitating a user's grip of the instrument.

4. The system according to claim 1, further comprising an angled intermediate section between the handle section and the head section.

5. The system according to claim 4, wherein the intermediate section is offset from a longitudinal axis of the elongate member by an angle of from substantially fifty to eighty degrees.

6. The system according to claim 4, wherein the handle section and the intermediate section define a substantially cylindrical body having a diameter that is greatest where the handle section begins proximate the first end of the member, and gradually decreases until the intermediate section terminates at the head section.

7. The system according to claim 1, wherein the phalange includes a substantially rounded tip and is contoured to engage a back side of a femur.

8. A surgical guide instrument for performing anterior cruciate ligament reconstruction comprising:
an elongate member having first and second ends;
a hand-graspable handle proximate the first end of the elongate member; and
a head portion proximate the second end of the elongate member, the head portion including a contoured phalange formed at a distal end of the head and an open-faced slot formed at a proximal end of the head, the slot including a guide wire entrance and a guide wire exit, the guide wire exit further including a stop member thereon, the phalange including a notch surface structured to engage the femoral intercondylar notch.

9. An instrument according to claim 8, wherein the contoured phalange is structured to anatomically conform to the femur.

10. The surgical guide instrument according to claim 8 further including a guide wire and a guide wire sheath, wherein said guide wire is received by said guide wire sheath.

11. The surgical guide instrument according to claim 10 wherein said guide wire sheath is structured to be received by said open-face slot adjacent said stop member.

12. The surgical guide instrument according to claim 11 wherein said stop member is structured to prevent said guide wire sheath from exiting the guide wire exit of said open-faced slot.

13. The surgical guide instrument according to claim 8, wherein said elongate body includes an intermediate portion positioned between the handle portion and the head section, wherein the intermediate portion angled to allow the surgical guide instrument to be leveraged against a posterior cruciate ligament.

14. The surgical guide instrument according to claim 8, wherein the body section is substantially cylindrical, and has a diameter that gradually decreases as the body section extends from the first end of the instrument toward the head section.

15. The surgical guide instrument according to claim 8, wherein the handle portion is contoured and includes a grippable surface for facilitating the user's handling of the instrument.

16. The surgical guide instrument according to claim 8, wherein the height of the stop member is greater than a width of the guide wire sheath.

17. A surgical instrument according to claim 8, wherein the instrument is constructed from a transparent material that allows a user to visualize the guide wire exit the guide wire exit.

18. A method of preparing a femur to receive a graft in an anterior cruciate ligament reconstruction on a human knee comprising:
(a) preparing a tibial tunnel;
(b) providing a surgical guide instrument including an elongate member having first and second ends;
  a hand-graspable handle proximate the first end of the elongate member; and
  a head portion proximate the second end of the elongate member, the head portion including a contoured phalange formed at a distal end of the head and an open-faced slot formed at a proximal end of the head, the slot including a guide wire entrance and a guide wire exit, the guide wire exit further including a stop member thereon;
(c) inserting the surgical guide instrument through a portal proximate a joint line between a tibia and a femur and advancing it into an intercondylar notch such that the guide wire entrance of said slot is positioned above an intraarticular aperture of the tibial tunnel;
(d) assembling a guide wire and a guide wire sheath wherein said guide wire is received by said sheath to form a guide wire assembly;
(e) grasping the guide wire assembly and manually advancing them through the tibial tunnel; inserting the head section through a portal proximate a joint line between the tibia and the femur;
(f) inserting the guide wire assembly into the through the open-faced slot and seating the sheath adjacent the stop member;
(g) advancing the surgical guide instrument and seated guide wire assembly into the posterior aspect of the intercondylar notch;
(h) causing the phalange to engage a posterior wall of a lateral femoral condyle such that the notch surface is pressed flush against the wall of the intercondylar notch;
(i) drilling the guide wire into the femur as it exits the guide wire exit of the slot;
(j) withdrawing the sheath from the guide wire assembly antegrade from the slot;
(k) pushing the surgical guide instrument posteriorly such that the guide wire exits the open-faced slot;
(l) removing the surgical guide instrument through the medial portal.

19. A system for use in ACL reconstruction comprising:
a surgical guide instrument including an elongate member having first and second ends, a hand-graspable handle proximate the first end of the elongate member, and a head portion proximate the second end of the elongate member, the head portion including a curved phalange formed at a distal end of the head and an open-faced slot formed at a proximal end of the head, the slot including a guide wire entrance and a guide wire exit, the guide wire exit further including a stop member thereon;
an angled intermediate section between the handle section and the head section, the intermediate section being offset from a longitudinal axis of the elongate member by an angle of from substantially fifty to eighty degrees, wherein the handle section and the intermediate section define a substantially cylindrical body having a diameter that is greatest where the handle section begins proximate the first end of the member, and gradually decreases until the intermediate section terminates at the head section;
a guide wire structured to be slidingly receivable in said open-faced slot; and
a guide wire sheath structured to be positioned over said guide wire and adjacent said stop member.

20. A system for use in ACL reconstruction comprising:
a surgical guide instrument including an elongate member having first and second ends, a hand-graspable handle proximate the first end of the elongate member, and a head portion proximate the second end of the elongate member, the head portion including a curved phalange formed at a distal end of the head and an open-faced slot formed at a proximal end of the head, the slot including a guide wire entrance and a guide wire exit, the guide wire exit further including a stop member thereon;
a guide wire structured to be slidingly receivable in said open-faced slot; and
a guide wire sheath structured to be positioned over said guide wire and adjacent said stop member, said stop member being structured to prevent said guide wire sheath from exiting the guide wire exit of said open-faced slot.

21. A surgical guide instrument for performing anterior cruciate ligament reconstruction comprising:
an elongate member having first and second ends;
a hand-graspable handle proximate the first end of the elongate member; and
a head portion proximate the second end of the elongate member, the head portion including a contoured phalange formed at a distal end of the head and an open-faced slot formed at a proximal end of the head, the slot including a guide wire entrance and a guide wire exit, the guide wire exit further including a stop member thereon; and
an intermediate portion positioned between the handle portion and the head section, wherein the intermediate portion is angled to allow the surgical guide instrument to be leveraged against a posterior cruciate ligament.

* * * * *